US006762227B1

(12) United States Patent
Elwing et al.

(10) Patent No.: US 6,762,227 B1
(45) Date of Patent: Jul. 13, 2004

(54) INHIBITION OF MARINE BIOFOULING OF SURFACES

(75) Inventors: Hans Elwing, Askim (SE); Lena Mårtensson, Kungälv (SE)

(73) Assignee: I-Tech AB, Billdal (SE)

( * ) Notice: Subject to any disclaimer, the term of this patent is extended or adjusted under 35 U.S.C. 154(b) by 0 days.

(21) Appl. No.: 09/889,447

(22) PCT Filed: Jan. 25, 2000

(86) PCT No.: PCT/SE00/00149

§ 371 (c)(1),
(2), (4) Date: Nov. 27, 2001

(87) PCT Pub. No.: WO00/42851

PCT Pub. Date: Jul. 27, 2000

(30) Foreign Application Priority Data

Jan. 25, 1999 (SE) ................................ 9900264

(51) Int. Cl.[7] .................. A01N 43/50; A01N 25/34; C09D 5/16
(52) U.S. Cl. ................. 524/106; 252/380; 523/122; 514/94
(58) Field of Search .................. 252/380; 523/122; 524/106; 514/94

(56) References Cited

U.S. PATENT DOCUMENTS

| 4,678,775 | A | 7/1987 | Nathanson |
| 4,783,457 | A | 11/1988 | Nathanson |

FOREIGN PATENT DOCUMENTS

| JP | 2020573 A | 1/1990 |
| JP | 3027178 A | 2/1991 |
| JP | 09-169607 | 6/1997 |
| WO | WO 95/05739 A1 | 3/1995 |
| WO | WO 98/05719 A1 | 2/1998 |

*Primary Examiner*—Kriellion A. Sanders
(74) *Attorney, Agent, or Firm*—Burns, Doane, Swecker & Mathis, L.L.P.

(57) ABSTRACT

The use of an aromatic compound substituted with at least one heterocyclic amine and possibly additional substituents, such as medetomidine and clonidine, or a functionally analogous derivative thereof, as an agent for the inhibition of marine biofouling on a surface, by application thereon of said compound, is disclosed. Also a method for inhibition of marine biofouling on a surface by application of said compound is disclosed.

21 Claims, No Drawings

INHIBITION OF MARINE BIOFOULING OF SURFACES

FIELD OF INVENTION

The present invention relates to inhibition of marine growth on or marine biofouling of surfaces in marine environments, and more particularly to the use of specific substances as a agent for prevention of marine biofouling of solid surfaces, and to a method of inhibiting marine biofouling of solid surfaces.

TECHNICAL BACKGROUND

With time, solid surfaces in marine environments will be covered with several different species of plants and animals. Such marine growth or biofouling is a considerable problem in the shipping business and other marine industries, such as aquatic cultures and marine oil and gas prospecting. Untreated ship hulls or other untreated underwater surfaces are rapidly fouled by growth thereon of marine plants and animals, and such growth highly increases friction, which in the case of ships among other things results in increased fuel consumption. To owners of leisure craft in Sweden and many other countries, the acorn barnacle is one of the most unwanted marine biofouling organisms. When fully grown, the acorn barnacle is responsible for a considerable amount of the biofouling-induced water resistance, and in addition, the acorn barnacle is difficult to remove by mechanical means from the surface on which it has attached itself.

One way of preventing marine biofouling of surfaces is to use paint comprising various types of toxic substances, such as tributyl tin oxide (TBT) or copper. The use of paints of this kind is, however, highly harmful to the environment and/or to individuals. For example, it has been found that oyster cultivations may be affected, and that the contents of such paints or toxicants are high in marine sedimentation. The use of these toxic substances thus is prohibited in many countries and more countries are expected to follow suit.

Among "non-toxic" methods are particularly noted high-pressure flushing of ship hulls or mechanical removal of the organisms. Most of these methods are, however, time-consuming and therefore expensive.

On the Swedish west coast, like on the North-Atlantic coasts generally, the settlement of the acorn barnacle (Balanus) is a problem of particular magnitude. The fully-grown acorn barnacle is an attaching crustacean that surrounds itself with hard calcareous plates and forms a volcano the size of about one centimeter and of high mechanical strength. The acorn barnacle has different stages of free-swimming larvae, the last stage of which is called cyprid. With the aid of protruding appendages (cirri), the larva scans solid surfaces for suitable locations on which to establish itself. In connection with the establishment a "glue" known as balanus cement is secreted from special glands on the appendages, by means of which the larva attach itself to the surface. After establishment, the animal undergoes a transformation or metamorphosis and becomes an adult individual.

SUMMARY OF THE INVENTION

The present invention relates to the removal of marine growth or biofouling in an ecologically acceptable manner.

One object of the invention is the use of an aromatic compound substituted with at least one heterocyclic amine and possibly also additional substituents, or a functionally analogous derivative thereof as an agent for the prevention of marine biofouling of a solid surface.

Another object of the invention is a method for the inhibition of marine biofouling of a solid surface, according to which method at least one aromatic compound which is substituted with at least one heterocyclic amine and possibly with additional substituents, or a functionally analogous derivative thereof, is applied on said surface.

The present invention has many advantages. For example, the substances in accordance with the invention are comparatively harmless compared with the toxic substances presently used in ship hull paints, such as tributyl tin oxide. Indeed, several of the substances in accordance with the invention are so harmless that they are approved as pharmaceutical preparations for internal use.

DETAILED DESCRIPTION OF THE INVENTION

As already mentioned, the present invention relates to the use of an aromatic compound substituted with at least one heterocyclic amine and possibly also additional substituents, or a functionally analogous derivative thereof, as an agent for the prevention of marine growth, known as biofouling, on a solid surface.

By the expression "aromatic compound" as used herein should be understood an organic compound comprising at least one flat ring having three conjugated double bonds. One example of an aromatic compound of this kind is benzene.

By the expression "heterocyclic amine" as used herein is to be understood a heterocyclic compound comprising an amino group ($-NH_2$) or a substituted amino group.

By the expression "functionally analogous derivative" of the compounds according to the invention as used herein is to be understood all structural and biological analogues of the compounds in accordance with the invention that have essentially the same settling-inhibiting effect on biofouling as the compounds in accordance with the invention.

The aromatic substituted compounds used in accordance with the invention are particularly suitable to prevent biofouling of the kind formed by settling crustacean organisms, particularly acorn barnacles and most particularly acorn barnacles of the genus Balanus, and by settling polychaetes, particularly the tube building polychaetes *Hydroides elegans*.

Acorn barnacles are hermaphrodites with internal fertilization. The pelagian larvae are called nauplius and feed on microorganisms of various kinds until they have stored sufficient nourishment to metamorphose into the last larval form, called cyprid larva. The cyprid larva is highly specialised to find a suitable solid surface. It has a highly developed sensorial system and proceeds by trial and error, "walking" across the surface with the aid of tentacles or cirri. The cirri also contain glands discharging a sticky protein secretion acting as a "glue". When the cyprid has found a suitable surface the glue production is taken over by two larger paired glands. The cyprid then metamorphoses into an adult individual. During this period the individual also grows from approximately 0.1 mm to one or a few centimeters. The establishment of the cyprid on the solid surface is known as settling.

The aromatic substituted compounds used in accordance with the invention preferably are imidazoles or imidazolines. The compounds most preferably used are medetomidine, (±)-4-[1-(2,3-dimethylphenyl)-ethyl]-1H- imidazole-mono-hydrogen chloride of formula I below, or clonidine, 2-(2,6-di-chloro-anilino)-2-imidazoline of formula II below.

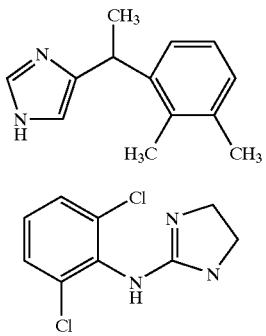

It is also possible to use a combination of several aromatic substituted compounds in accordance with the invention or derivatives thereof.

An explanation that in no way restricts the invention of the reason why these compounds are efficient in inhibiting biofouling could be that they disturb or block the transmission of signals to the effector cells needed in order for e.g. cyprid larvae, acorn barnacles and hydrozoans to establish themselves or settle.

The aromatic substituted compounds used in accordance with the invention preferably are enclosed in a polymer, and preferably a polymer allowing slow or delayed release of the aromatic substituted compounds. One example of a suitable polymer is an acrylic polymer. The polymer is then applied on the surface in question, and in water the compounds in accordance with the invention will be released slowly from the polymer. The attachment of marine biofouling substances to the surface thus will be disturbed in a manner preventing settlement.

The aromatic substituted compounds in accordance with the invention are intended to inhibit biofouling in marine environments.

The aromatic substituted compounds in accordance with the invention are for example highly suitable for prevention of biofouling of ship hulls. For this application it may be suitable to incorporate the compound in paint intended for application on ship hulls. It is also possible to incorporate the compound in cleaning solutions intended for washing ship hulls or to rinse the ship hull with a solution of the aromatic substituted compound in accordance with the invention in order to thus achieve a biofouling-inhibiting effect. It appears as if the compounds in accordance with the invention somehow bind to the surface and in this manner produce a long-lasting effect. The aromatic substituted compounds could also be used in combination with treatments of a mechanical nature, such as high-pressure flushing, in order to increase the effect further.

The aromatic substituted compounds in accordance with the invention are highly suitable for prevention of biofouling of piping through which flows seawater. In this case it is possible to pass the aromatic substituted compound through the pipes in pulses and in this manner produce a remaining biofouling-inhibiting effect. The treatment may be repeated when needed.

The invention will be illustrated further by means of the following examples which are in no way intended to restrict the scope of protection of the invention.

EXAMPLES

In the examples below are used medetomidine marketed by Orion Pharma, Helsinki, Finland, and clonidine marketed by Sigma Chemical Co., USA.

Example 1

This example illustrates the settlement-inhibiting effect of one compound in accordance with the invention, medetomidine, on cyprid larvae. Cyprid larvae from *Balanus improvisus* were transferred to Petri dishes containing seawater from the Swedish west coast and medetomidine in various concentrations (0.1 nM, 1 nM, 10 nM, 100 nM and 1 $\mu$M). In addition, for control purposes, cyprid larvae were transferred to a Petri dish containing seawater only. After 11 days the cyprids were counted and classified as either 1) settled (established) on the surface of the Petri dish, 2) swimming, i.e. living, not established, or 3) dead. The result is set forth in Table 1. The results in the table are expressed in percentage of the total number of organisms in each group (=n). From this experiment appears that the number of established larvae decreased upon increased concentration of medetomidine. The experiment also shows that the number of dead cyprids did not increase upon increased contents of medetomidine, which testifies to the non-toxic nature of medetomidine.

TABLE 1

| Concentration of medetomidine (nM) | Settled (%) | Swimming (%) | Dead (%) |
|---|---|---|---|
| 0 (control) | 74 | 22 | 3.4 |
| 0.1 | 52 | 48 | 0 |
| 1 | 1.5 | 98 | 0 |
| 10 | 0 | 100 | 0 |
| 100 | 0 | 100 | 0 |
| 1000 | 0 | 100 | 0 | n = 55 ± 7

Example 2

This example corresponds to Example 1 with the exception that medetomidine was replaced by clonidine in the concentrations defined in Table 2 below. The results appear from Table 2.

TABLE 2

| Concentration of clonidine (ng/ml) | Settled (%) | Swimming (%) | Dead (%) |
|---|---|---|---|
| 0 (control) | 58.9 | 37.5 | 3.5 |
| 0.027 | 36.7 | 65.7 | 0 |
| 0.27 | 22.3 | 77.7 | 0 |
| 2.7 | 1.8 | 96.5 | 1.7 |
| 27 | 0 | 98.5 | 1.5 |
| 270 | 0 | 91.7 | 8.3 | n = 20 ± 2

Example 3

This example shows the considerable tendency of medetomidine to bind to solid surfaces. Petri dishes of hydrophilic polystyrene were filled with a solution of medetomidine in varying concentrations (0 ng/ml 10 ng/ml, 1 μg/ml and 10 μg/ml). Like in Example 1, one Petri dish with no medetomidine was used as control. After a 24 hour incubation period in room temperature the dishes were cleaned thoroughly with seawater. The dishes were then incubated with cyprid larvae in amounts of approximately 20 larvae/dish. Readings were taken under microscope after 7 days, and the larvae were classified as either settled, free-swimming or dead. It is worth noting that a significant reduction of the number of settled acorn barnacles was found, also at very low medetomidine incubation concentrations.

TABLE 3

| Concentration of medetomidine (ng/ml) | Settled (%) | Swimming (%) | Dead (%) |
|---|---|---|---|
| 0 (control) | 54.4 | 45.6 | 0 |
| 1 | 6.2 | 93.8 | 0 |
| 10 | 0 | 100 | 0 |
| 1000 | 0 | 100 | 0 |
| 10000 | 0 | 100 | 0 | n = 20 ± 2

Example 4

Example 3 was repeated, with the difference that Petri dishes of hydrophobic polystyrene were used instead of hydrophilic dishes.

TABLE 4

| Concentration of medetomidine (ng/ml) | Settled (%) | Swimming (%) | Dead (%) |
|---|---|---|---|
| 0 (control) | 58.6 | 41.4 | 0 |
| 1 | 63.1 | 36.9 | 0 |
| 10 | 33.3 | 65 | 2.1 |
| 1000 | 0 | 100 | 0 |
| 10000 | 0 | 97.9 | 2.1 | n = 20 ± 2

Example 5

This experiment illustrates the effect of mixing a compound in accordance with the invention with a standard paint. Medetomidine was added to an acrylate-based paint formula to a concentration of 0.02% by weight (or 170 μg/ml). The paint was then applied on 10 test surfaces dimensioned 10×10 $cm^2$. The surfaces were allowed to dry at room temperature and were then mounted on racks, which were placed at a depth of about one meter in a bay in the sea offshore from Strömstad, Sweden, and were allowed to remain there during August and September of 1999. After 2, 4 and 8 weeks, respectively, the test surfaces were removed from the sea and the number of acorn barnacles (*Balanus improvisus*) were counted. As control surfaces were used surfaces coated with an acrylate-based paint to which no medetomidine had been added. The result of this experiment is shown in Table 6 below. The results show that a significant reduction of the number of acorn barnacles on the test surfaces was obtained compared with the control surfaces, which verifies the functional practicability of the invention also when used as a paint additive.

TABLE 5

| | Number of *Balanus improvisus*/10 $cm^2$ | |
|---|---|---|
| Time | Control plates | Medetomidine-treated plates |
| 2 weeks | 157.5 ± 25.6 | 4.63 ± 1.04 |
| 4 weeks | 137.7 ± 30.8 | 5.6 ± 1.4 |
| 8 weeks | 479.7 ± 31.7 | 148.1 ± 16.24 |

Example 6

This example illustrates the settling-inhibiting effects of a compound in accordance with the invention, medetomidine, on tube building polychaetes (*Hydroides elegans*). The polychaete larvae were incubated for two days in Petri dishes containing sea water and were then classified as either settled, free swimming or dead, like in Example 1. The water originated from the coast outside Sydney, Australia, and the experiment was carried out in May 1999. The results are shown in Table 7 below. The table shows that medetomidine has a significant inhibiting effect on settling of polychaete larvae in the concentration span of from 0.1 nM to 100 μM. It also shows that toxic effects appear in the span from 100 nM to 100 μM.

TABLE 6

| Concentration of medetomidine (nM) | Settled (%) | Swimming (%) | Dead (%) |
|---|---|---|---|
| 0 (control) | 43.8 | 56.2 | 0 |
| 0.1 | 9.3 | 88.4 | 2.3 |
| 1 | 5.4 | 89.2 | 5.4 |
| 10 | 0 | 95.6 | 4.4 |
| 100 | 0 | 80 | 20 |
| 1000 | 0 | 54.3 | 45.7 |
| 100 000 | 0 | 0 | 100 | n = 15 ± 3

What is claimed is:

1. A method of inhibiting marine biofouling on a solid surface, wherein at least one compound chosen from the group consisting of (±)-4-[1-(2,3dimethyl phenyl)-ethyl]-1H-imidazole-mono-hydrogen chloride, 2-(2,6-di-chloro-anilino)-2-imida-zoline or functionally analogos derivatives thereof, is applied on said surface.

2. A method according to claim 1, wherein said marine biofouling consists of settling crustaceans.

3. A method according to claim 2, wherein said crustaceans are acorn barnacles.

4. A method according to claim 3, wherein said crustaceans are acorn barnacles of the species Balanus.

5. A method according to claim 1, wherein said marine biofouling consists of settling polychaetes.

6. A method according to claim 5, wherein said polychaetes are *Hydroides elegans*.

7. A method according to claim 1, wherein said solid surface is a surface normally located in a marine environment.

8. A method according to claim 7, wherein said surface is a ship hull.

9. A method according to claim 7, wherein said surface is a sea water pipe installation.

10. A method according to claim 9, wherein said solid surface is a surface normally located in a marine environment.

11. A method according to claim 10, wherein said solid surface is a surface normally located in a marine environment.

12. A method according to claim 11, wherein said solid surface is a surface normally located in a marine environment.

13. A method according to claim 12, wherein said solid surface is a surface normally located in a marine environment.

14. A method according to claim 13, wherein said solid surface is a surface normally located in a marine environment.

15. A method according to claim 10, wherein said surface is a ship hull.

16. A method according to claim 11, wherein said surface is a ship hull.

17. A method according to claim 12, wherein said surface is a ship hull.

18. A method according to claim 13, wherein said surface is a ship hull.

19. A method according to claim 14, wherein said surface is a ship hull.

20. A method according to claim 10, wherein said surface is a sea water pipe installation.

21. A method according to claim 1, wherein said compound is used in combination with a polymer allowing delayed release of said compound.

* * * * *